United States Patent [19]

Li

[11] 4,156,098

[45] May 22, 1979

[54] PURIFICATION OF BISPHENOL-A

[75] Inventor: Ming K. Li, Schenectady, N.Y.

[73] Assignee: General Electric Company, Schenectady, N.Y.

[21] Appl. No.: 910,437

[22] Filed: May 30, 1978

[51] Int. Cl.$^2$ ............................................. C07C 37/34
[52] U.S. Cl. .................................................... 568/724
[58] Field of Search ................................ 568/724, 728

[56] References Cited

U.S. PATENT DOCUMENTS

| 2,791,616 | 5/1957 | Luten | 568/724 |
|---|---|---|---|
| 2,959,622 | 11/1960 | Grimme et al. | 568/724 |
| 3,627,846 | 12/1971 | Meyer | 568/724 |
| 3,936,507 | 2/1976 | Ligorati et al. | 568/724 |

*Primary Examiner*—Norman Morgenstern
*Attorney, Agent, or Firm*—Joseph T. Cohen; Charles T. Watts

[57] ABSTRACT

Impure bisphenol-A can be purified by treatment of a phenol adduct of the latter with methylene chloride and then recovering the purified bisphenol-A.

5 Claims, No Drawings

PURIFICATION OF BISPHENOL-A

This invention is concerned with the purification of 2,2-bis(4-hydroxyphenyl)propane (hereinafter identified as "bisphenol-A" or "BPA"). More particularly, the invention is directed to a method for recovering bisphenol-A in a purified state from a mixture of the latter and impurities derived from the acid-catalyzed condensation of phenol and acetone, which method comprises intimately admixing a phenol adduct of bisphenol-A with methylene chloride and then recovering and isolating the precipitated bisphenol-A in a highly purified state substantially free of impurities which originally were present.

Bisphenol-A is commercially prepared by reacting phenol and acetone in the presence of an acidic material such as sulfuric acid, hydrochloric acid, etc. As a result of carrying out this reaction, the bisphenol produced is accompanied by undesirable impurities such as the 2-(4-hydroxyphenyl)-2-(2-hydroxyphenyl)propane (hereinafter identified as "o,p-isomer") having the formula

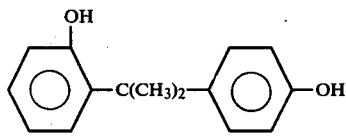

as well as other impurities including phenol itself used in making the bisphenol-A, a trishydroxyphenyl compound of the formula

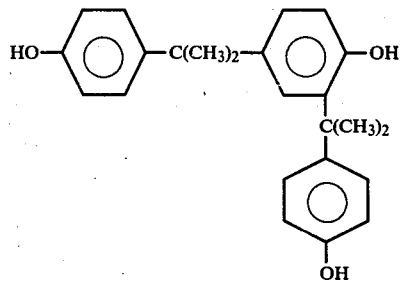

(hereinafter identified as "BPX-I"), small amounts of other impurities such as the compound having the formula

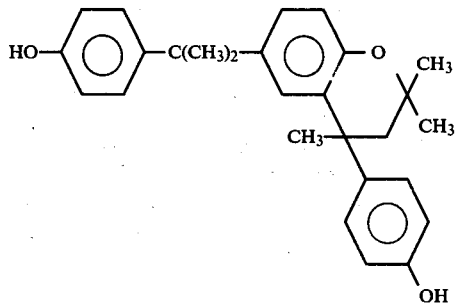

(hereinafter identified as "BPX-II"), etc.

Since bisphenol-A is used in making polycarbonate resins by reaction of the latter with either phosgene or diphenyl carbonate, or for making epoxy resins, both resins being used extensively in commercial applications involving molding, casting, and sheet forming purposes, it is highly important that the monomeric bisphenol-A used to make such resins be as pure as possible in order to avoid adverse effects on the properties of the polymers thus obtained.

The preparation of the bisphenol-A by the reaction of phenol and acetone often leads to an adduct in which there is 1 mol of phenol per mol of the bisphenol-A together with any excess phenol which may have been used for reaction purposes. One method for working with this adduct to arrive at a purified bisphenol-A is described in Luten U.S. Pat. No. 2,791,616 issued May 7, 1957. According to this patent, the adduct obtained as a result of carrying out the initial reaction in the presence of the acidic condensation catalyst, uses an excess amount of water within a well-defined temperature range which serves to liberate the phenol from the adduct with the result that essentially all the phenol is dissolved in the water while substantially all the bisphenol-A remains behind in the solid state. However, this process suffers from several disadvantages. Excessive amounts of water are usually required. Also, the water obtained containing the phenol, whether liberated from the adduct or the excess amount used in carrying out the initial condensation reaction, is in the form of a mixture which requires considerable processing and expenditure of energy in order to recover the phenol so that it can be used again for reaction with the acetone.

Another purification processing step which has been employed after the adduct is broken is to subject the bisphenol-A to high temperature distillation to separate the latter from the impurities. In the process of using the high temperatures required (even under vacuum conditions) some of the BPA is lost through degradation and tar formation, thus contributing to a process which does not permit optimum yields of the bisphenol-A in a highly purified state.

Unexpectedly, I have discovered that I can treat the bisphenol-A-phenol adduct initially with methylene chloride whereby the latter surprisingly has been found capable of breaking the adduct, thereby causing solution of the impurities and the release of phenol into the methylene chloride. The bisphenol-A remaining behind is in a highly purified state requiring only a minimum of further treatment for maximum yield and optimum purity.

I have discovered that the treatment with the methylene chloride is advantageously carried out at a relatively low temperature usually below 60° C. (e.g., from 20° to 50° C.) for a time ranging from about 15 minutes to 5 or more hours. Thereafter, the mother liquor of the mixture (which usually requires only the formation of a slurry) which consists of the methylene chloride, phenol, and impurities, plus small amounts of biphenol-A, can be filtered (e.g., at a temperature of from 30° to 40° C.) to yield crystalline bisphenol-A in a highly purified state requiring only a minimum of further processing to obtain the desired degree of purity. I have additionally found that by using the methylene chloride with a controlled temperature profile, the crystals of bisphenol-A on the average are larger than usual, which permits greater purity and greater ease in separation by filtration, and any processing of these larger crystals again requires only a minimum of treatment to obtain the optimum yield and purity of the bisphenol-A.

The term "bisphenol-A-phenol adduct" as used herein is intended to mean either (1) the adduct which is obtained as a result of the reaction of the phenol and the acetone in the presence of an acidic condensation catalyst, as well as (2) a preformed adduct which is made from impure bisphenol-A which has been treated with a sufficient amount of phenol to form the adduct. The molar concentration of the adduct consists of 1 mol of the bisphenol-A to 1 mol of phenol, and, on a weight basis, represents approximately 70 percent of the bisphenol-A and about 30 percent of the phenol. Regardless of whether the initial reaction product adduct or the subsequently preformed adduct is used, the methylene chloride treatment as described above is equally as effective in cleaving the adduct, removing the impurities, and providing a highly purified bisphenol-A in good yield with a minimum of processing.

It should be recognized that some percentage of the bisphenol-A (e.g., from 10 to 25% of the original bisphenol-A in the adduct) is still present in the methylene chloride mother liquor and wash liquor. I have found that by a still further reduction in temperature, for example, within a temperature range of about 15° to 30° C., most of the bisphenol-A in the mother liquor crystallizes out in the form of the adduct, leaving behind the methylene chloride with the phenol and impurities dissolved therein. Thereafter, this adduct can be treated with either additional methylene chloride or recycled back into the initial adduct treatment with methylene chloride, thereby providing a continuous process for obtaining highly purified bisphenol-A in good yields from the adduct with a minimum of processing steps and without the need for subjecting the major portion of the bisphenol-A to high temperature distillations which have been found to affect adversely the purity and yield of the bisphenol-A.

In preparing the adduct for treatment with the methylene chloride, the adduct, normally in combination with the excess phenol, is usually first filtered to remove undesirable solid products which interfere with attainment of the desired objectives of the invention. The adduct is then mixed thoroughly with a sufficient amount of the methylene chloride at the appropriate temperature and stirred for a time long enough to cause the system to reach equilibrium. The amount of methylene chloride used with the adduct can range, on a weight basis, from 0.5 to 20 or more parts of the former per part of the adduct. On a weight basis, I may advantageously employ from about 2 parts to 8 parts of the methylene chloride per part of the adduct. The more methylene chloride used, the lower the temperature at which optimum results are realized; this of course requires handling of larger volumes of liquid.

The temperature at which the adduct is combined with the methylene chloride and thereafter heated is fairly low, and is usually below 75° C. I have successfully carried out the claimed process at temperatures within the narrow range of between 20° and 45° C. Thereafter, the mixture of the adduct and the methylene chloride is filtered without further cooling, e.g., at a temperature of from 30° to 40° C.

The methylene chloride solution is removed, usually by filtering off the solid crystals of bisphenol-A. If desired, the isolated bisphenol-A can be washed with an additional amount of methylene chloride to ensure the ultimate removal of most of the impurities which at this stage are in minimal amount, principally clinging to the surfaces of the bisphenol-A crystals, and exercise little if any effect on the quality of polymers made from the bisphenol-A.

In order that those skilled in the art may better understand how the present invention may be practiced, the following examples are given by way of illustration and not by way of limitation.

EXAMPLE 1

In this example, a bisphenol-A-phenol adduct was prepared by dissolving isolated crude bisphenol-A (obtained from the initial reaction of phenol and acetone) in a large excess of phenol at a temperature of about 95° C. and allowing the solution to cool to about 40° to 50° C. The adduct which precipitated out was removed by filtration from the mother liquor which consisted mostly of phenol and impurities. This procedure allowed for a close simulation of the adduct that would be obtained in a bisphenol-A manufacturing plant. The biphenol-A-phenol adduct which was recovered by filtration was then mixed thoroughly with an adequate amount of methylene chloride at a chosen temperature for a period of time sufficient to cause the system to reach equilibrium. At this point, the mixture of ingredients was filtered leaving solid bisphenol-A and small amounts of impurities behind. The bisphenol-A was further washed with sufficient methylene chloride to remove residual impurities which adhered to the BPA crystalline surfaces. The following Table I shows the proportions of ingredients used, the temperatures initially employed to dissolve the impure solid adduct, the stirring time in hours to ensure complete miscibility of the adduct with the methylene chloride, the temperature at which filtration was carried out after adding the methylene chloride, and the weight ratio of the methylene chloride to the adduct used in the wash step, the temperature of the wash solvent being ambient (room) temperature in each instance.

TABLE I

|  | Test Number | | | |
| --- | --- | --- | --- | --- |
|  | 1A | 1B | 2 | 3 |
| CH$_2$Cl$_2$/Adduct (weight basis) | 2:1 | 1.5:1$^a$ | 4:1 | 4:1 |
| Initial temp. of solution | 40° C. | 40° C. | 37° C. | 37° C. |
| Filtration temp. °C. (mixture/funnel) | 40/40 | 40/40 | 37/25 | 37/37 |
| Stirring time hours | 2.5 | 1.5 | 1 | 0.5 |
| Wash (wt. CH$_2$Cl$_2$/Adduct) | — | 1:1 | 1:1 | 2:1 |
| No. of washes | — | 2X | 2X | 1X |
| Appearance Bisphenol-A | white crystals | white crystals | white crystals | white crystals |

$^a$The solid adduct employed in Test Number 1B was that collected from 1A and shows a two-stage process permitting the use of less CH$_2$Cl$_2$ than if all the CH$_2$Cl$_2$ was employed at one time.

The crystalline bisphenol-A materials were analyzed by liquid chromatography to determine the weight percents of the desired bisphenol-A and other impurities which have been referred to above. For comparison, the crude adduct which was initially used and then treated with the methylene chloride was also analyzed with the following results as shown in Table II. Where no figures are given, this means that no amount of the cited impurity was detected.

TABLE II

| Ingredients Present | $^b$% Crude Adduct | % Test No. 1A | % Test No. 1B | % Test No. 2 | % Test No. 3 |
| --- | --- | --- | --- | --- | --- |
| Bisphenol-A | 67.20 | 75.358 | 99.125 | 97.13 | 99.24 |
| o,p-BPA | 0.705 | — | — | 0.05 | — |
| $^a$L.D. & C.D. combined | 0.444 | — | — | 0.23 | 0.26 |

TABLE II-continued

| Ingredients Present | $^b$% Crude Adduct | % Test No. 1A | % Test No. 1B | % Test No. 2 | % Test No. 3 |
|---|---|---|---|---|---|
| BPX-I | 0.026 | — | — | 0.13 | — |
| BPX-II | 0.289 | — | — | — | — |
| Phenol | 31.14 | 24.642 | 0.875 | 2.06 | 0.49 |

$^a$Two impurities having formulas

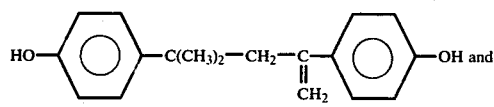 and

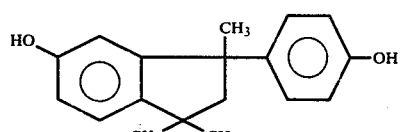

$^b$No methylene chloride treatment

It will of course be understood by those skilled in the art that in addition to the conditions and proportion of ingredients employed in the foregoing examples, other conditions of admixture, filtering, washing and separating, and ratios of the adduct to the methylene chloride may be employed within the scope of the intended invention as more particularly described above.

What I claim as new and desire to secure by Letters Patent of the United States is:

1. The method of recovering 2,2-bis(4-hydroxyphenyl) propane in a purified state from a mixture of the latter and impurities derived from the acid catalyzed condensation of phenol and acetone, which comprises (1) combining an adduct of phenol and the above-identified impure dihydroxy-diphenyl propane with methylene chloride to effect intimate admixture of the adduct and the methylene chloride, (2) allowing the dihydroxy-diphenyl propane to precipitate from the methylene chloride component, and (3) separating the precipitated dihydroxy-diphenyl propane in the form of a highly purified crystalline product.

2. The process as in claim 1 wherein the admixture of the adduct and the methylene chloride is carried out with stirring at a temperature below 60° C.

3. The process as in claim 1 wherein the mother liquor obtained as a result of removing the precipitated dihydroxy-diphenyl propane is further treated with methylene chloride and the mixture subjected to reduced temperatures to effect precipitation of additional amounts of the dihydroxy-diphenyl propane.

4. The process as in claim 1 wherein the precipitated dihydroxy-diphenyl propane is washed with methylene chloride to provide still higher purity product.

5. The process as in claim 1 wherein the filtration step required to obtain the precipitated dihydroxy-diphenyl propane is carried out at a temperature of from 30° to 40° C.

* * * * *